US006987998B2

(12) United States Patent (10) Patent No.: US 6,987,998 B2
Kalgren et al. (45) Date of Patent: Jan. 17, 2006

(54) CARDIAC RHYTHM MANAGEMENT PATIENT REPORT

(75) Inventors: James Kalgren, Lino Lakes, MN (US); Mitchell Lanz, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 336 days.

(21) Appl. No.: 09/795,830

(22) Filed: Feb. 28, 2001

(65) Prior Publication Data

US 2002/0156389 A1 Oct. 24, 2002

(51) Int. Cl.
*A61B 5/04* (2006.01)
(52) U.S. Cl. ...................................... 600/523; 600/509
(58) Field of Classification Search ............... 600/523, 600/509, 528, 489; 340/33; 705/3, 2; 607/5, 607/14, 4
See application file for complete search history.

(56) References Cited

U.S. PATENT DOCUMENTS

| | | | | |
|---|---|---|---|---|
| 4,531,527 A | * | 7/1985 | Reinhold et al. | ........... 600/509 |
| 4,800,883 A | | 1/1989 | Winstrom | ............... 128/419 D |
| 4,809,697 A | | 3/1989 | Causey, III et al. | ... 128/419 PT |
| 4,825,869 A | | 5/1989 | Sasmor et al. | ......... 128/419 PT |
| 4,850,357 A | | 7/1989 | Bach, Jr. | ................ 128/419 D |
| 4,964,410 A | * | 10/1990 | Leahey et al. | ............... 600/509 |
| 4,998,531 A | | 3/1991 | Bocchi et al. | .......... 128/419 D |
| 5,029,082 A | * | 7/1991 | Shen et al. | .................. 600/512 |
| 5,065,315 A | | 11/1991 | Garcia | .................... 364/413.01 |
| 5,111,816 A | | 5/1992 | Pless et al. | ........... 128/419 PG |
| 5,129,392 A | | 7/1992 | Bardy et al. | ............ 128/419 D |
| 5,215,083 A | | 6/1993 | Drane et al. | ............ 128/419 D |
| 5,217,021 A | | 6/1993 | Steinhaus et al. | ........... 128/702 |
| 5,225,976 A | | 7/1993 | Tawil | ........................ 364/401 |
| 5,267,155 A | | 11/1993 | Buchanan et al. | ..... 364/419.14 |
| 5,277,188 A | | 1/1994 | Selker | ........................ 128/696 |
| 5,279,293 A | | 1/1994 | Andersen et al. | ............... 607/5 |
| 5,292,341 A | | 3/1994 | Snell | ........................... 607/30 |
| 5,307,817 A | * | 5/1994 | Guggenbuhl et al. | ....... 600/508 |
| 5,311,874 A | | 5/1994 | Baumann et al. | ........... 128/705 |
| 5,312,441 A | | 5/1994 | Mader et al. | ................... 607/5 |
| 5,343,869 A | * | 9/1994 | Pross et al. | ................... 600/301 |
| 5,411,530 A | | 5/1995 | Akhtar | ......................... 607/14 |
| 5,421,830 A | | 6/1995 | Epstein et al. | ................ 607/30 |
| 5,513,645 A | | 5/1996 | Jacobson et al. | ........... 128/710 |
| 5,549,654 A | | 8/1996 | Powell | ........................ 607/32 |
| 5,581,460 A | | 12/1996 | Kotake et al. | .............. 395/203 |
| 5,607,460 A | | 3/1997 | Kroll et al. | ................... 607/30 |
| 5,652,842 A | * | 7/1997 | Siegrist et al. | ................. 705/2 |
| 5,704,371 A | | 1/1998 | Shepard | ..................... 128/897 |
| 5,724,985 A | * | 3/1998 | Snell et al. | ................. 600/510 |
| 5,725,559 A | * | 3/1998 | Alt et al. | ........................ 607/5 |
| 5,817,137 A | | 10/1998 | Kaemmerer | ................. 607/59 |
| 5,978,707 A | | 11/1999 | Krig et al. | .................... 607/14 |
| 5,991,729 A | | 11/1999 | Barry et al. | ................... 705/3 |

(Continued)

FOREIGN PATENT DOCUMENTS

EP 0491649 6/1992

(Continued)

*Primary Examiner*—Daniel Robinson
(74) *Attorney, Agent, or Firm*—Schwegman, Lundberg, Woessner & Kluth, P.A.

(57) ABSTRACT

A patient oriented report from an implantable medical device such as a cardiac rhythm management device, e.g. a cardiac pacemaker or cardioverter/defibrillator, and a system and method for producing the same. The report provides the patient with various information regarding the treatment, type of device, manufacturer, physician, device settings, or device status.

30 Claims, 4 Drawing Sheets

U.S. PATENT DOCUMENTS

| | | | |
|---|---|---|---|
| 6,014,630 A | 1/2000 | Jeacock et al. | 705/3 |
| 6,016,446 A | 1/2000 | Belalcazar | 607/13 |
| 6,026,363 A | 2/2000 | Shepard | 705/3 |
| 6,067,471 A | 5/2000 | Warren | 607/5 |
| 6,067,523 A | 5/2000 | Bair et al. | 705/3 |
| 6,076,015 A | 6/2000 | Hartley et al. | 607/20 |
| 6,091,990 A | 7/2000 | Hsu et al. | 607/5 |
| 6,108,577 A | 8/2000 | Benser | 600/517 |
| 6,112,117 A | 8/2000 | KenKnight et al. | 607/5 |
| 6,208,974 B1 * | 3/2001 | Campbell et al. | 705/3 |
| 6,283,761 B1 | 9/2001 | Joao | 434/236 |
| 6,289,248 B1 | 9/2001 | Conley et al. | 607/59 |
| 6,304,849 B1 | 10/2001 | Uecker et al. | 705/3 |
| 6,415,175 B1 | 7/2002 | Conley et al. | 600/523 |
| 6,418,340 B1 | 7/2002 | Conley et al. | 600/523 |
| 6,430,439 B1 | 8/2002 | Wentkowski et al. | 607/9 |
| 6,440,082 B1 | 8/2002 | Joo et al. | 600/528 |
| 6,473,638 B2 * | 10/2002 | Ferek-Petric | 600/523 |
| 6,493,579 B1 | 12/2002 | Gilkerson et al. | 607/5 |
| 6,581,038 B1 | 6/2003 | Mahran | 705/3 |
| 6,584,445 B2 | 6/2003 | Papageorge | 705/3 |
| 6,665,558 B2 | 12/2003 | Kalgren et al. | 600/510 |

FOREIGN PATENT DOCUMENTS

| | | |
|---|---|---|
| EP | 0558353 | 9/1993 |
| EP | 0565084 | 10/1993 |
| EP | 0711531 | 5/1996 |

* cited by examiner

GUIDANT

THE WORLD LEADER IN CARDIAC RHYTHM MANAGEMENT

"PATIENTS NAME" PACEMAKER REPORT

DEVICE TYPE
DEVICE MODEL NUMBER
DEVICE SERIAL NUMBER

LEAD MANUFACTURER
LEAD MODEL NUMBERS
LEAD SERIAL NUMBERS

REASON FOR IMPLANT: SLOW HEART RATE IN THE LOWER CHAMBERS OF YOUR HEART.
YOUR PACEMAKER IS DELIVERING A PACING OUTPUT XX% OF THE TIME.
THE LOWEST HEART RATE YOUR PACEMAKER WILL ALLOW IS XX BEATS PER MINUTES.
YOUR PACEMAKER WILL PACE FASTER WHEN YOU ARE ACTIVE.

PHYSICIAN:                    PHONE NUMBER:

DATE OF NEXT FOLLOW-UP:

FOR MORE INFORMATION VISIT US AT WWW.GUIDANT.COM

Fig. 3

GUIDANT

THE WORLD LEADER IN CARDIAC RHYTHM MANAGEMENT

"PATIENTS NAME" AICD REPORT

DEVICE TYPE
DEVICE MODEL NUMBER
DEVICE SERIAL NUMBER

LEAD MANUFACTURER
LEAD MODEL NUMBERS
LEAD SERIAL NUMBERS

REASON FOR IMPLANT: VENTRICULAR FIBRILLATION, OCCASIONAL VERY FAST HEART RATE.
YOU HAVE RECENTLY RECEIVED XX LIFE SAVING SHOCK(S) TO TREAT VENTRICULAR FIBRILLATION.
YOUR DEVICE IS DELIVERING A PACING OUTPUT XX% OF THE TIME.
THE LOWEST HEART RATE YOUR PACEMAKER WILL ALLOW IS XX BEATS PER MINUTES.
YOUR PACEMAKER WILL PACE FASTER WHEN YOU ARE ACTIVE.

PHYSICIAN:                    PHONE NUMBER:

DATE OF NEXT FOLLOW-UP:

FOR MORE INFORMATION VISIT US AT WWW.GUIDANT.COM

Fig. 4

CARDIAC RHYTHM MANAGEMENT PATIENT REPORT

This invention pertains to cardiac rhythm management report for patients and to methods and systems for producing same.

BACKGROUND

Medical devices are implanted in patients to address specific health problems. Cardiac rhythm management devices are one type of implantable medical device and are commonly referred to as pacemakers. Cardiac rhythm management devices provide pacing and defibrillation functions to patients with corresponding heart problems. Systems communicate with the cardiac rhythm device to program same and retrieve data from the cardiac rhythm management device for diagnostic and treatment purposes.

Some patients desire to know a great deal about their medical problem, the implanted medical device, and exactly how the medical device treats their problem. Unfortunately, many patients lack basic knowledge of anatomy and physiology which is necessary to understand implant therapy concepts. Consequently, medical care providers may spend a significant amount of time explaining the reasons for implanting the medical device and how the medical device treats the patient's problem. However, medical care providers have a high degree of medical training and may explain the operation of the device using medical terms which may not be fully understood by a patient. A patient desiring information may not ask follow up questions until he\she understands the medical treatment provided by the implanted medical device. On the other hand, some medical care providers have acquired a skilled bed side manner in addition to their medical training and explain the medical treatment provided by the implant in non-medical, easy to understand terms. Unfortunately during times of illness, a patient may not feel well enough to concentrate on the explanation and remember same.

SUMMARY OF THE INVENTION

It is desirable to provide a patient with information about an implanted medical device, such as a cardiac rhythm management device, without the need for interpretation by trained medical personnel. According to one embodiment of the present invention, a patient report generating system produces a report specifically for the patient. This would enable a patient, for example, to refer to the report for information regarding the implanted medical device and where to find additional information without waiting until the next visit with the physician.

Accordingly, in one embodiment, the present invention is a patient report generating system providing reports about an implanted medical device, such as a cardiac rhythm management device, for example a cardiac pacemaker or an implantable cardioverter/defibrillator.

Another embodiment of the invention is a cardiac patient report generating system including a cardiac rhythm management device, a programming unit communicating with the cardiac rhythm management device, and an output device producing a report for a patient.

In another embodiment, the invention is a patient report providing information regarding a medical device, the information being understandable to a non-medically trained patient. In another embodiment, the report includes medical device identifying information, medical device manufacturer information, physician information, and information specific to the relationship between the medical device and patient.

These and other embodiments, aspects, advantages, and features of the present invention will be set forth in part in the description which follows, and will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims.

BRIEF DESCRIPTION OF THE DRAWINGS

FIG. 3 is another embodiment of a patient report.

FIG. 4 is another embodiment of a patient report.

DESCRIPTION OF THE INVENTION

In the following detailed description of the invention, reference is made to the accompanying drawings which form a part hereof, and in which is shown, by way of illustration, specific embodiments in which the invention may be practiced. These embodiments are described in sufficient detail to enable those skilled in the art to practice the invention. Other embodiments may be utilized and structural, logical, and electrical changes may be made without departing from the scope of the present invention.

Figure 1:
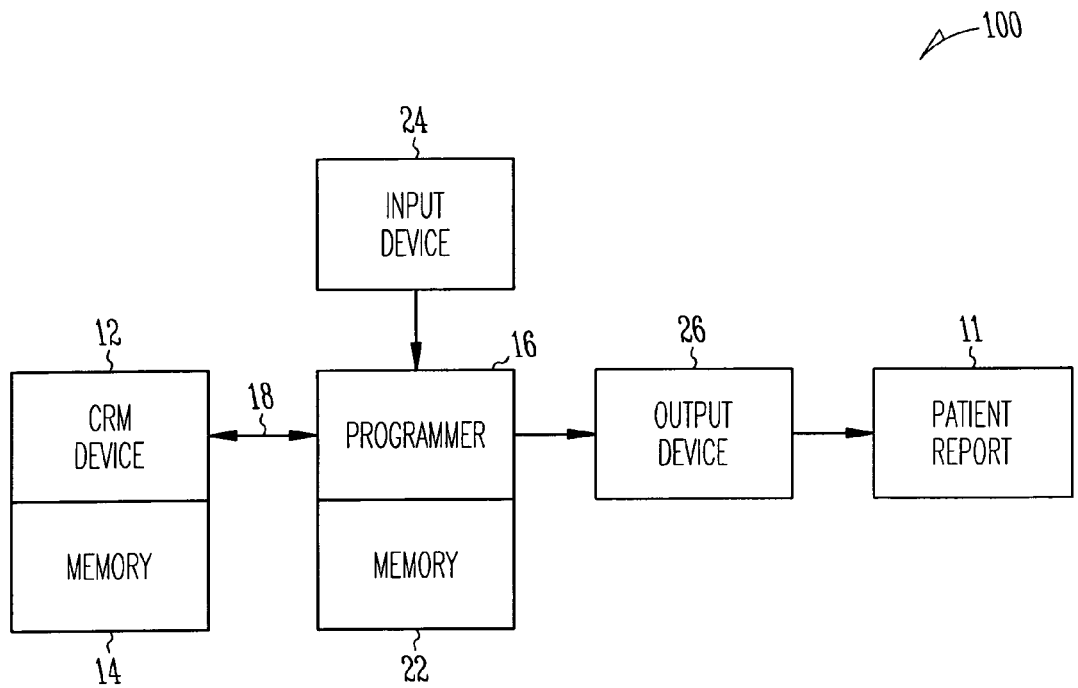
FIG. 1 is a system diagram of a patient report generating system incorporating the present invention.

FIG. 1 shows a system diagram of a patient medical report generating system 10 for generating a patient report 11. System 10 includes a cardiac rhythm management device ("CRM device") 12, which is a microprocessor-based pacemaker with defibrillation and/or antitachycardia pacing capability and includes a data storage module 14, for example RAM, ROM, EEPROM, etc. Examples of such devices are found in U.S. Pat. Nos. 6,112,117; 6,108,577; 6,091,990; 6,076,015; 6,067,471; 6,016,446; and 5,978,707, all assigned to the present assignee, and all herein incorporated in their entirety by reference. The data storage module 14 stores data representing the manufacturer name, contact information, type of device, device serial number, or other manufacturer identification information. Module 14 may also store component manufacturer information such as the name of the lead manufacturer, the lead model number, or the lead serial number. Module 14 further stores operational parameters of CRM device 12 which include the number of shock pulses applied by CRM device 12 to the patient's heart, the duty rate of pacing the patient's heart, the lowest allowable heart rate allowed by the pacemaker, etc. The overall operation of the device is controlled by a system program running from the memory module 14.

CRM device 12 communicates with a programmer 16 via a bidirectional communication path 18. Path 18 is typically wireless to allow programmer 16 to read data from the CRM device 12 and transmit programming instructions to the CRM device with CRM device 12 implanted in a patient. Programmer 16 includes a memory 22 which typically comprises a ROM for program storage, a RAM for data storage, and a memory device for long term data storage, such as a hard drive or removable machine readable media.

An input device 24, such as a touch screen or keyboard, allows the medical personnel installing the CRM device to input data into programmer 16. The input data can include patient name, diagnosis, CRM device type, CRM device operation parameters, physician name, physician contact information, and next patient appointment.

Figure 2:
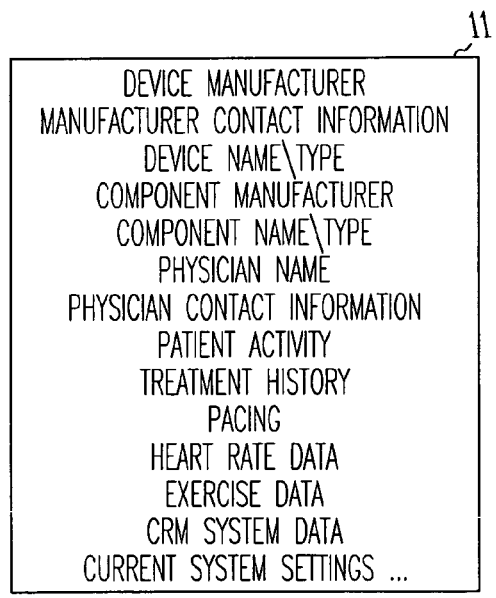
FIG. 2 is a patient report according to the present invention.
Figure 5:
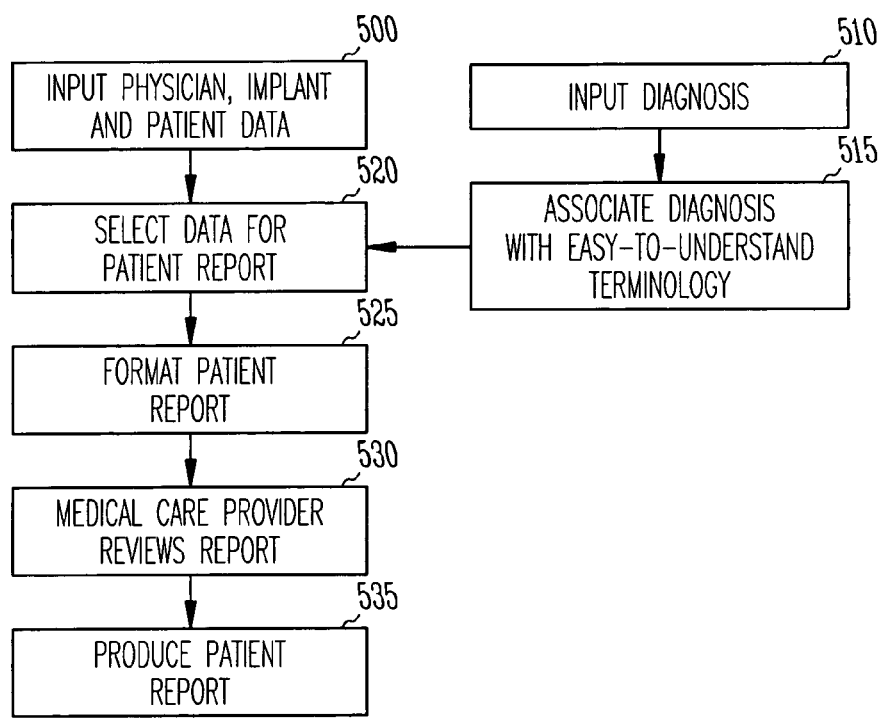
FIG. 5 is a flow chart of a method for producing a patient report.

An output device 26 is connected to programmer 16 and produces a patient report 11 based on data sent to it by the programmer. Examples of the output device 26 are printers, disk drives, CD writers, data storage writers, etc. In one particular embodiment, output device 26 is a printer which produces a printed patient report 11 that includes various information that may be of interest to the patient. Referring to FIG. 2, such information includes device manufacturer, manufacturer contact information, implant device name, model and serial number, lead manufacturer, lead type, physician name, physician contact information, patient activity data, pacing data, heart rate data, exercise data, CRM system data, and current CRM device settings. Additional data that relates to the patient and/or the CRM device may also be stored in the programmer and/or the CRM device. The programmer includes a default patient report which has specific datafields. However, medical personnel running the programmer can accept the default patient report or select which data is provided on the patient report 11, either in a printed form or displayed on a monitor. Thus, the medical personnel can filter unrelated data or unnecessary data from the patient report.

Reference is now made to FIGS. 3 and 4 which show different embodiments of formatted patient reports 11A and 11B. Report 11A is a pacemaker report which is produced when the implanted CRM device 12 is a pacemaker. Report 11A includes seven distinct fields. The report could have greater or fewer fields depending on the amount of data to be produced for a patient report 11 associated with a particular implanted device. Moreover, if one of the shown fields is not selected by the medical personnel or is not applicable to the implanted device, then it would be removed from the patient report 11 so as to not imply that information is missing from the report or provide a patient with information that does not apply to his\her particular implanted device. The uppermost field on patient report 11A is the manufacturer field 41, which may include manufacturer name, promotional statements, and manufacturer contact information. A patient report identification field 43 is directly below manufacturer field 41. Field 43 may include patient name, another patient identifier, and the type of report, in FIG. 3 it is shown as a pacemaker report. An implanted device field 45 is directly below patient report identification field 43 and is subdivided into a left subfield 46 including device information, like type, model number and serial number, and right subfield 47 including component information, like lead manufacturer, model number and serial number. A medical information field 49 is directly below the implanted device field 45 and includes information explaining, preferably in easy to understand, plain English terminology (examples of which are provided below), the reason for the implant, what the implant does, how often the implant activates, the implant settings, and other information which would be relevant for the particular therapy provided by the implant. In the FIG. 3 embodiment, field 49 explains that the implant was needed to account for a slow heart rate in the lower chambers of the patient's heart. Field 49 goes on to explain that the pacemaker delivers pacing output a predetermined percentage of time and the lowest heart allowed by the pacemaker is a predetermined number of beats per minute, both the predetermined percentage and the predetermined number of beats are CRM device operational parameters determined by the physician. Field 49 also provides additional information which a patient receiving a pacemaker may want to know, for example the pacemaker will pace the patient's heart faster when the patient is active. A physician information field 51 is directly below the medical information field 49. Field 51 includes the physician's name and contact information, here illustrated as the physician's phone number. Field 51 also includes the date of the patient's next appointment. A second manufacturer field 53 is directly below the physician information field 51. Field 53 includes additional manufacturer information such as its web address. Field 53 may also provide a reference to further information regarding pacing and defibrillation as well as information regarding the implanted CRM device. While the above description of the patient report positions fields 41–53 relative to each other, it will be understood that the layout of the fields may be changed.

One aspect of the patient report 11 is to provide easy to understand language or "plain English" terminology of the treatment provided by the implant to the patient. The plain English terminology is intended to be understood by non-medically trained patients and accurately describe the treatment provided by the CRM device. However, medical terminology need not be completely removed from the patient report 11. Field 49 of FIG. 4 shows both the medical diagnosis of ventricular fibrillation and its corresponding plain English description of an occasional very fast heart rate. Modern CRM devices treat a variety of medical conditions and thus the system must provide a corresponding number of plain English interpretations. The programmer memory 22 includes a lookup table in which plain English terminology is associated with the medical treatments provided by the implant device, in the described embodiments the CRM device 12. One embodiment of the look up table is shown in table 1.

TABLE 1

| Medical Terminology | Plain English |
| --- | --- |
| Atrial Tachycardia with Block | Lack of synchronization between heart chambers causing very fast heart rate |
| Atrial Flutter | Occasional very fast, repeating heart rate |
| Atrial Fibrillation | Occasional very fast heart rate |
| Atrioventricular Nodal Reentrant | Abnormally fast heart rhythm |
| Atrioventricular Block | Lack of synchronization between upper and lower heart chambers |
| Chaotic Atrial Rhythm | Irregular heart beat |
| Multifocal Atrial Tachycardia | Irregular heart beat |
| Sick Sinus Syndrome | Slow heart rate |
| Sinus Tachycardia | Very fast heart rate |
| Sinus Arrest | Pause in a normal heart rhythm |
| Sinus Bradycardia | Slow heart rate |
| Sinus Node Dysfunction | Incorrect heart rhythm signal |
| Tachycardia-Bradycardia Syndromes | Occasional fast or slow heart rates |
| Ventricular Tachycardia | Fast heart rate |
| Ventricular Flutter | Occasional very fast, repeating heart rate |
| Ventricular Fibrillation | Occasional very fast, irregular heart rate |
| Wolff-Parkinson-White syndrome | Fast heart rate |

The above table is not exhaustive of all diagnosis and their corresponding plain English phrase. Moreover, the plain English phrases may also include other words or be interpreted differently.

When implanting a device, the medical personnel typically input information using input device 24 into programmer 16 to create and store medical records as well as program the implant. The medical personnel typically record the physician's name, the patient's name, the manufacturer name, and implant model and serial numbers (step 500). The diagnosis is also stored in the medical records (step 510), sometimes in medical terminology such as those in Table 1 and sometimes as diagnosis codes. If the diagnosis is input and stored as codes in memory 22, then the look up table would associate the code with either the medical terminology and then to the corresponding plain English phrase or directly associate the diagnosis codes with the corresponding plain English phrase. It is within the scope of the present invention to access previously stored data representing certain information for the patient report, for example, the physician name may be stored in the programmer memory and can be accessed each time the programmer produces patient report 11. Thus, some information need not be entered each time a patient report is produced. The present system accesses the stored diagnosis and associates it with non-medical, plain English terminology written for a patient (step 515). The information for the patient report is selected by the medical care provider (step 520) and formatted by the programmer (step 525), typically in a standard format stored in the programmer memory 22, for example one of the formats illustrated in FIGS. 2–4. The medical care provider can review and revise the patient report to fit the individual patient's needs (step 530). Once the patient report meets the medical care provider's approval, the programmer sends the report to output device 26 which produces patient report 11 (step 530).

It will be understood that these steps are modifiable for a particular programmer and/or medical records storage system of the physician. For example, the programmer may access a medical records database and download physician name and phone number, diagnosis, and the next appointment information. The programmer may also store numerous model numbers for the implant device in memory, which is displayed to the medical care provider in a menu format. The medical care provider would merely select the implant device's model number from this menu. In another embodiment, the programmer reads the implant information directly from the implant device itself or the implant information may be coded on the packaging of the implant, for example bar coded, which can be read directly into the programmer by an input device, for example a scanner. In another embodiment, the data for the patient report and the desired format can be selected for all of a physician's patients. The need for the medical care provider to review the selected data, format of the report, etc. need only be performed once and stored in the programmer as a physician specific default. In an alternative to a physician specific report, a report associated with a specific diagnosis may also be stored in the programmer which is the default selection for a specific diagnosis.

Both the patient and the medical care provider benefit by patient report 11 by same providing the patient with easy to understand explanations of the diagnosis and therapy. The patient report 11 further provides the patient with contact information for additional sources of information relative to their implant device and general medical knowledge regarding their condition.

An additional benefit of patient report 11 is it contains vital health information that is readily accessible and portable with the patient. As a result when a patient with an implant is away from his/her doctor, for example on vacation, if the patient takes the patient report 11 along and has a medical emergency, then the attending medical provider will know some details about the implant and the patient's physician who implanted the device.

Although the invention has been described in conjunction with the foregoing specific embodiments, many alternatives, variations, and modifications will be apparent to those of ordinary skill in the art. For example, it will be recognized that the format of the patient report may be different than those illustrated in FIGS. 3 and 4. Such alternatives, variations, and modifications are intended to fall within the scope of the following appended claims.

What is claimed is:

1. A cardiac patient report generating system, comprising:
   a cardiac rhythm management device;
   a programming unit communicating with said cardiac rhythm management device; and
   an output device connected to said programming unit, said output device producing a report for a patient, wherein said report directly informs a patient about said cardiac rhythm management device in terminology easy for a non-medically trained patient to interpret.

2. The system of claim 1, wherein said output device is a printer and said report is a printed report for a patient.

3. The system of claim 1, wherein said output device includes a write device and the report for a patient is stored on a removable storage media.

4. The system of claim 3, wherein said write device is an electromagnetic read/write device and the report is written electromagnetically to a removable electromagnetic storage media which is given to a patient.

5. The system of claim 3, wherein said write device is an electro-optical read/write device and the report is written electro-optically to a removable electro-optically storage media which is given to a patient.

6. The system of claim 1, wherein said report includes at least one of patient's name, physician's name, cardiac rhythm management device manufacturer, cardiac rhythm management device model number, and cardiac rhythm management device serial number.

7. The system of claim 6, wherein said cardiac rhythm management device manufacturer, cardiac rhythm management device model number, and cardiac rhythm management device serial number are stored in said cardiac rhythm management device and read by said programming unit.

8. The system of claim 7, wherein said programming unit formats said cardiac rhythm management device manufacturer, cardiac rhythm management device model number, and cardiac rhythm management device serial number into a data stream, and transmits same to said. output device.

9. The system of claim 1, wherein said report includes at least one of a physician's name, physician's contact information and a date of a patient's next visit to the physician.

10. The system of claim 1, wherein said cardiac rhythm management device includes leads and said report includes at least one of lead manufacturer, lead model number, and lead serial number.

11. The system of claim 1, wherein said cardiac rhythm management device is implantable in a patient and is selected from a group consisting of a cardiac pacemaker, a cardioverter/defibrillator, and a combination pacemaker/defibrillator.

12. The system of claim 1, wherein said cardiac rhythm management device is implanted in a patient and said report includes a reason for implantation.

13. The system of claim 12, wherein the reason for implantation is on said report in brief medical terminology and in plain English terminology for a non-medically trained patient's understanding.

14. The system according to claim 1, wherein said cardiac rhythm management device is a pacing device and said report includes at least one of pacing duty rate and lowest heart rate setting of the pacing device.

15. The system according to claim 1, wherein said report includes information regarding operation of said cardiac rhythm management device when a patient is active.

16. The system according to claim 1, wherein said cardiac rhythm management device is a cardioverter/defibrillator and said report includes heart shock application data.

17. The system according to claim 1, wherein said report includes a manufacturer name of said cardiac rhythm management device and manufacturer contact information.

18. The system according to claim 17, wherein said manufacturer information includes a global computer system address.

19. A medical device adapted for implantation into a patient, and a report providing information regarding said medical device, said information being understandable to a non-medically trained patient, said report comprising:
   medical device identifying information;
   medical device manufacturer information;
   physician information; and
   information specific to a relationship between said medical device and a patient.

20. The report according to claim 19, wherein said medical device identifying information includes at least one of device model number, device serial number, and device type.

21. The report according to claim 19, wherein said medical device manufacturer information includes at least one of manufacturer name, manufacturer address, manufacturer telephone number, and manufacturer global computer network address.

22. The report according to claim 19, wherein said physician information includes at least one of physician name, physician phone number, physician address, and next appointment date.

23. The report according to claim 19, wherein said information specific to a relationship between said medical device and patient includes at least one selected from a set comprising: a reason for implantation of said medical device in terms understandable to non-medically trained patients, number of treatments by said medical device, active duty time of said medical device, and setting parameters of said medical device.

24. The medical device according to claim 19 comprising a cardiac rhythm management device.

25. A method for generating an implanted cardiac rhythm device report for a patient, wherein said report is understandable to a non-medically trained patient, comprising:
   compiling implanted medical device identifying information;
   compiling medical diagnosis information;
   composing the medical diagnosis information in terminology understandable to non-medically trained person; and
   producing a report for a patient containing implanted medical device identifying information and composed medical diagnosis information.

26. The method of claim 25, wherein compiling implanted medical device information includes inputting manufacturer name and manufacturer contact information into a computer system and outputting the manufacturer name and the contact information in the report for patient.

27. The method of claim 25 wherein compiling medical diagnosis information includes retrieving the diagnosis information from a database.

28. The method of claim 27, wherein retrieving the medical diagnosis information from the database includes reading a diagnosis code from a database stored in a memory of a computer system.

29. The method of claim 28, wherein composing the medical diagnosis information includes associating the diagnosis code with a plain English interpretation stored in a database in a memory of a computer system.

30. The system of claim 1, wherein said report directly informs a patient about said cardiac rhythm management device absent interpretation by medical personnel.

* * * * *